US012496201B2

(12) United States Patent
Simpson

(10) Patent No.: US 12,496,201 B2
(45) Date of Patent: Dec. 16, 2025

(54) MEDICAL DEVICE RELEASE APPARATUS, SYSTEM AND METHOD OF USE

(71) Applicant: Vascutek Limited, Renfrewshire (GB)

(72) Inventor: Graeme Simpson, Glasgow (GB)

(73) Assignee: Vascutek Limited, Renfrewshire (GB)

(*) Notice: Subject to any disclaimer, the term of this patent is extended or adjusted under 35 U.S.C. 154(b) by 1054 days.

(21) Appl. No.: 17/601,231

(22) PCT Filed: Apr. 8, 2020

(86) PCT No.: PCT/GB2020/050912
§ 371 (c)(1),
(2) Date: Oct. 4, 2021

(87) PCT Pub. No.: WO2020/208349
PCT Pub. Date: Oct. 15, 2020

(65) Prior Publication Data

US 2022/0160528 A1 May 26, 2022

(30) Foreign Application Priority Data

Apr. 8, 2019 (GB) ..................................... 1904922

(51) Int. Cl.
*A61F 2/95* (2013.01)

(52) U.S. Cl.
CPC ......... *A61F 2/95* (2013.01); *A61F 2002/9511* (2013.01)

(58) Field of Classification Search
CPC ................ A61F 2/95; A61F 2002/9511; A61F 2002/9505; A61F 2002/9534; A61F 2/2427; A61F 2/011; A61F 2002/0072; A61F 2/2644; A61F 2002/2484; A61B 2017/1205; A61B 2017/12054
See application file for complete search history.

(56) References Cited

U.S. PATENT DOCUMENTS 6,468,298 B1 * 10/2002 Pelton ....................... A61F 2/95 606/198
2013/0289703 A1 10/2013 Kinkade et al.
2014/0135907 A1 * 5/2014 Gallagher ................. A61F 2/95 623/2.11
2014/0236278 A1 8/2014 Argentine et al.
2022/0160528 A1 5/2022 Simpson

FOREIGN PATENT DOCUMENTS

JP 2000/262362 A 9/2000
WO WO-2010/137583 A1 12/2010
WO WO-2012/024325 A1 2/2012
WO WO-2020/208348 A1 10/2020

* cited by examiner

*Primary Examiner* — Melanie R Tyson
*Assistant Examiner* — Rachel S Highland
(74) *Attorney, Agent, or Firm* — Foley Hoag LLP; Stephen J. Kenny; Nicole A. Bustos-Pomerantz

(57) ABSTRACT

The present invention concerns a medical device delivery apparatus, the apparatus comprising: a head element (11) at a proximal end of the apparatus, the head being configured for extending through the medical device and projecting proximally therefrom; the head element having one or more hook elements (13) for engaging a control loop coupled to the medical device, wherein the one or more hook elements are axially fixed in relation to the head element.

17 Claims, 3 Drawing Sheets

MEDICAL DEVICE RELEASE APPARATUS, SYSTEM AND METHOD OF USE

RELATED APPLICATIONS

This application is a § 371 national-stage application based on PCT/GB20/50912, filed Apr. 8, 2020; which claims the benefit of priority to Great Britain (UK) Patent Application 1904922.0, filed on Apr. 8, 2019.

The present invention relates to a medical device release apparatus and a method of use thereof.

Figure 1:
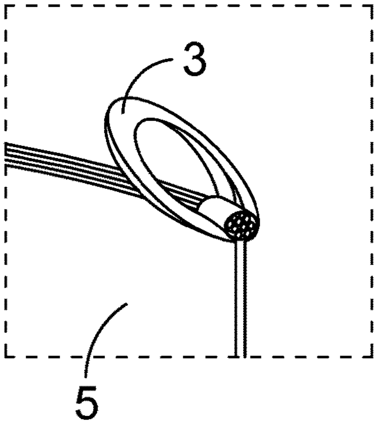
Figure 2:
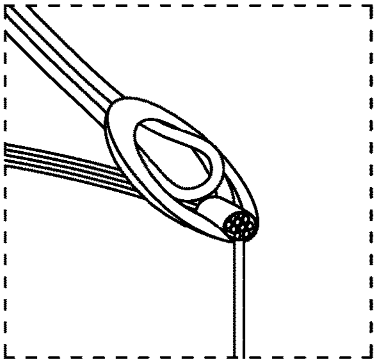
Figure 3:
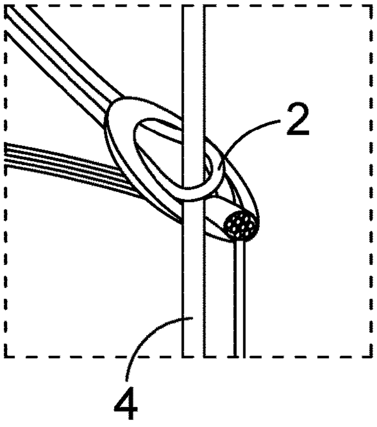

In this regard, medical devices such as endovascular stent devices are generally attached to their delivery system using a combination of control loop, eyelet and release wire. As shown in FIGS. 1 to 3, this connection is achieved by threading the free end of a control loop 2 of a control thread through an eyelet 3 with the other end being fixed to the tip of the delivery system. A release wire 4 is then passed through the open loop of the control thread, created when the control thread is passed through the eyelet, to prevent it from being pulled back through the eyelet.

The medical device 5 is released from the delivery system by removing the release wire 4, which allows the control loop 2 to pull back through the eyelet, freeing the device from the delivery system.

This arrangement can cause issues if the release wire is damaged and cannot be removed from the control loop. This prevents the user from being able to remove the delivery system from the patient without additional bail out procedures or a full conversion to open surgery.

Issues can also occur if the user forgets to remove the release wire before attempting to remove the delivery system. This causes the device to migrate from the intended sealing zone, disrupting the seal and potentially damaging the vessel in the process.

The present invention provides an apparatus and method, which seek to alleviate the problems of such known arrangements.

According to the present invention there is provided a medical device delivery apparatus, the apparatus comprising: —a head element at a proximal end of the apparatus, the head being configured for extending through the medical device and projecting proximally therefrom; the head element having one or more hook elements for engaging a control loop coupled to the medical device, wherein the one or more hook elements are axially fixed in relation to the head element.

In this manner, the medical device can be released at the same time as the delivery system is withdrawn without additional mechanical operation of the apparatus.

Preferably, the one or more hook elements are forward facing, with their free end extending in a direction towards the proximal end of the head element.

Conveniently, the head element has two hook elements.

Preferably, the hook elements are provided at diametrically opposite sides of the head element.

Conveniently, the one or more hook elements extend proximally to project radially outwardly from the longitudinal profile of the head element.

Preferably, the one or more hook elements are provided at a distal end of the head element.

Conveniently, the one or more hook elements each take the form of an inclined slot, open at a proximal end and closed at a distal end.

Preferably, each slot has a tapering profile.

Conveniently, the head element comprises a head body and a head plate, the head plate being coupled to a distal end of the head body to define said one or more hook elements between the head body and the head plate.

Preferably, the head body is chamfered at its distal end, to define said one or more hook elements.

Conveniently; the apparatus further comprises one or more attachment points for an end of a control loop.

Preferably, the one or more attachment points are provided on the head element proximally of the one or more hook elements.

Conveniently, the one or more hook elements are moveable between deployed and un-deployed positions.

Preferably, the one or more hook elements are pivotable between the deployed and undeployed positions.

Conveniently, the one or more hook elements are retractable so as to be substantially flush with the longitudinal profile of the apparatus.

Preferably, the one or more hook elements are profiled so that rotation of the head element promotes release of any control loop engaged by the one or more hook element.

Conveniently, the one or more hook elements comprise an angled section having a radially extending portion, the radially extending portion being configured to engage a control loop.

The apparatus preferably further comprises alignment means for aligning said one or more hook elements with one or more eyelets of medical device.

According to a further aspect of the present invention there is provided a medical device deployment system for deploying a medical device comprising: —medical device delivery apparatus having a head element at a proximal end of the apparatus, the head being configured for extending through the medical device and projecting proximally therefrom, the head element having one or more hook elements for engaging a control loop coupled to the medical device, wherein the one or more hook elements are axially fixed in relation to the head element.

According to a yet further aspect of the present invention there is provided a method of deploying a medical device using the delivery apparatus or deployment system of any preceding claim, the method comprising the steps: —passing said delivery apparatus through the interior of the medical device so that it protrudes from a proximal end thereof; coupling the medical device and one or more hook elements of the delivery apparatus using one or more control loops; advancing the apparatus to the deployment site; deploying the medical device at the site; and retracting the delivery apparatus, the one or more control loops releasing from the one or more hook elements, wherein the one or more hook elements are axially fixed in relation to the head element.

Preferably, said one or more control loops are attached to the head element of the delivery apparatus, pass through one or more eyelets provided to said medical device and then pass around said one or more hook elements before passing again through the one or more eyelets.

Conveniently, the one or more control loops are attached to the medical device, and pass around the one or more hook elements.

Preferably, the medical device has an undulating proximal end profile, the one or more control loops being attached to proximal peaks of the medical device.

Conveniently, the one or more hook elements are moved to facilitate release the one or more control loops.

Preferably, the one or more hook elements are pivoted rearwardly to facilitate release the one or more control loops.

Conveniently, the head element is rotated about its longitudinal axis to facilitate release the more or more control loops.

Embodiments of the present invention will now be described by way of example and with reference to the accompanying drawings, of which: —

Figures 6A, 6B, 6C:
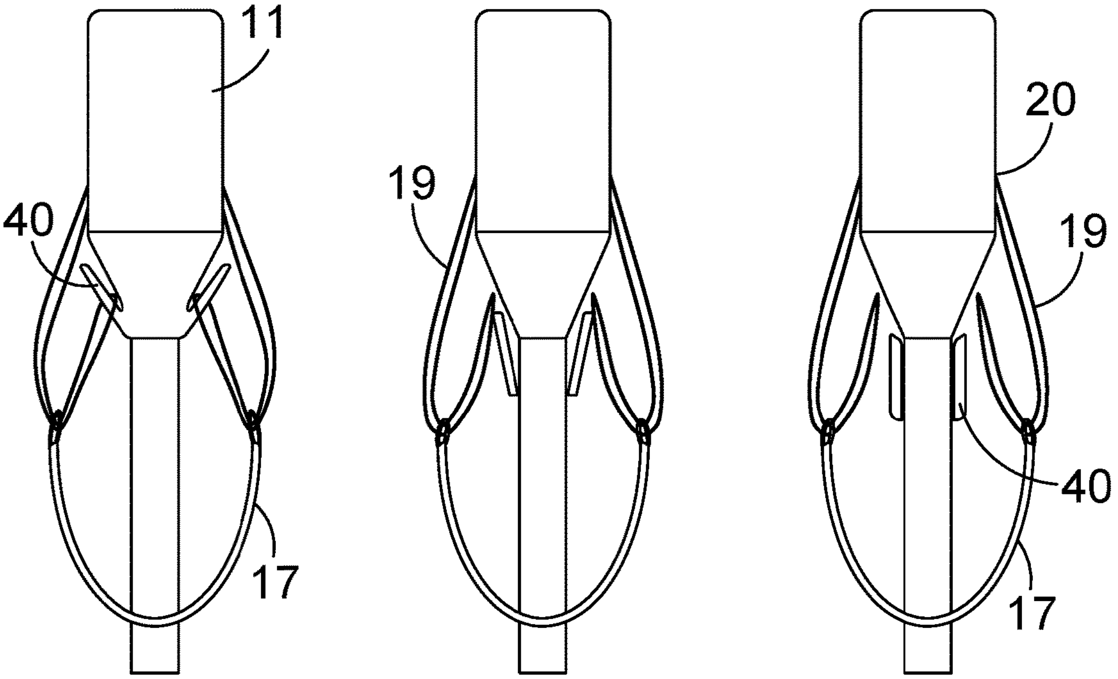
Figure 7A:
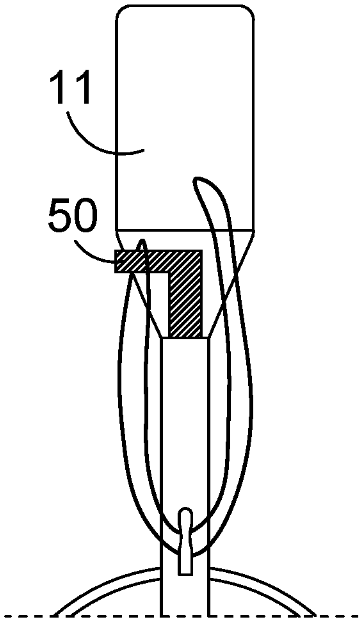
Figure 7B:
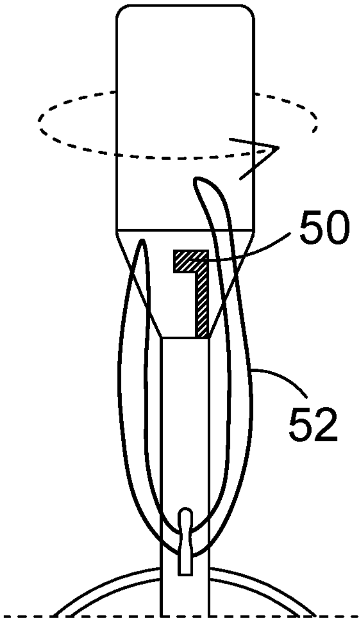

FIGS. 1 to 3 show a known arrangement for delivering a medical device to a site;

FIGS. 4*a* to 4*d* show a first embodiment of the present invention;

FIGS. 5*a* to 5*e* show a second embodiment of the present invention;

FIGS. 6*a* to 6*c* show a third embodiment of the present invention; and FIGS. 7*a* and 7*b* show a fourth embodiment of the present invention.

FIGS. 1 to 3 are discussed above and relate to a conventional delivery system for an endovascular device. Such systems can experience issues where the release wire is damaged or where the user forgets to remove it before attempting to remove the delivery system.

The present invention hence seeks to provide a medical device delivery system that does away with the need for release wire.

In this respect, as shown in FIGS. 4*a* to 4*d*, the delivery apparatus 10 comprises a tip or head element 11 at the proximal end of a longitudinal shaft 12. The head element has hook elements 13 that project radially outwardly and forwardly towards the proximal end of the head element. The hook elements may be formed in any suitable manner, and in the present embodiment are formed by chamfering the distal end of the head element and coupling a plate 14 thereto, in order to form slots 15. As shown, the ends 16 of the plates preferably project radially outwardly of the general outer longitudinal profile of the head element 11.

As shown, in use the head element is positioned to extend through the interior of a medical device 17, such as an endovascular stent, so that the head element 11 projects out of its proximal end. For clarity, the structure of the medical device is not shown in detail in the figures but may comprise an expandable stent device having an undulating proximal end denoted by reference 17. In the embodiment of FIGS. 4*a* to 4*d*, control loops 19 are attached at one end to the head element at attachment points 20 above the hook elements, namely closer to the proximal end of the head element.

Each control loop extends rearwardly and passes through an eyelet 21 coupled to the medical device. The loop then returns back to the head element to be looped around hook element 11 before returning to the eyelet and then up towards the proximal end of the apparatus.

Figure 4A:
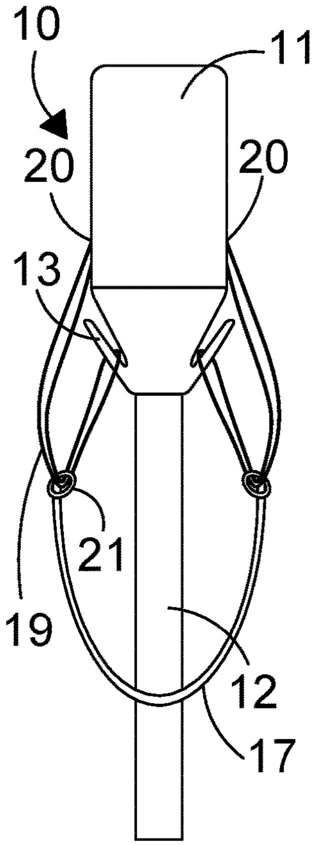

FIGS. 4*a* to 4*d* show the progression of the head element relative to the medical device 17. In FIG. 4*a*, the medical device has been moved to the correct position in relation to the site where it can be fixed in position. This may be by expanding the device so that it seals against the internal surfaces of a vessel in which it is being deployed.

Figure 4B:
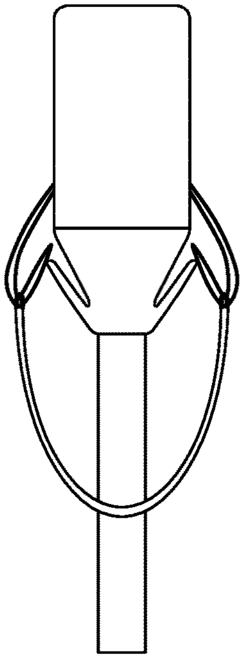
Figure 4C:
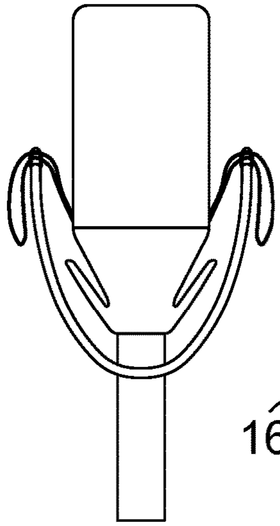
Figure 4D:
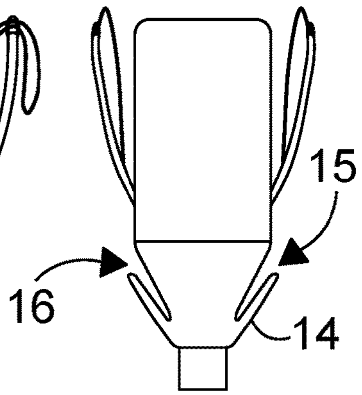
Figures 5A, 5B, 5C, 5D, 5E:
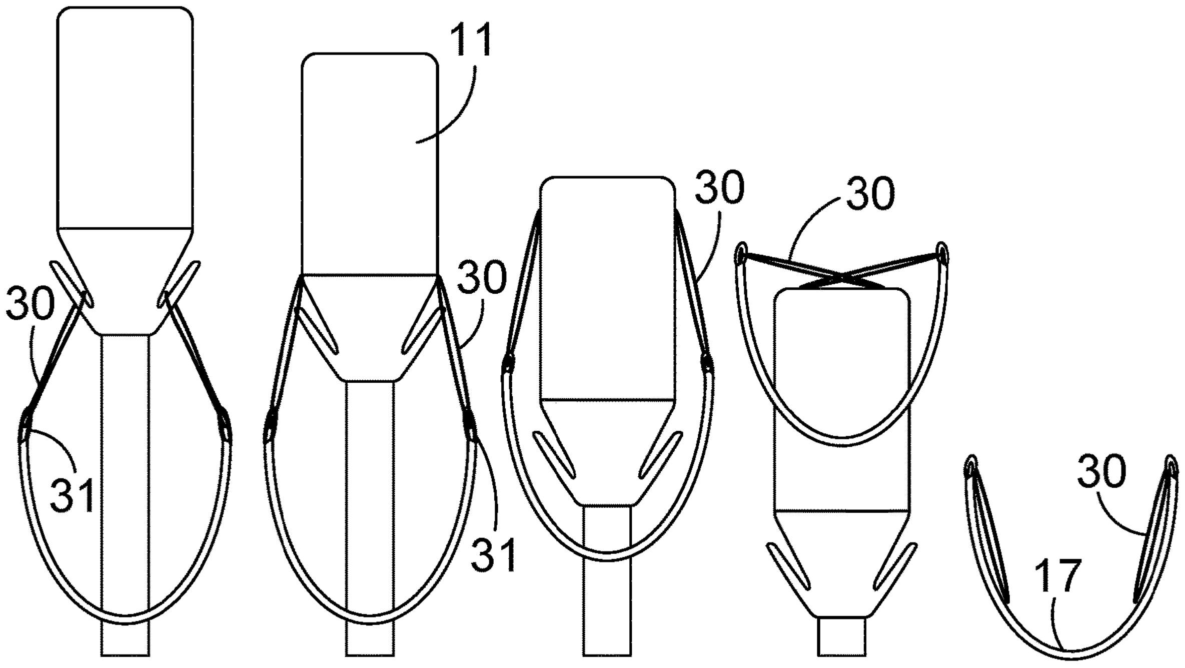

Once correctly fixed in position, the delivery apparatus is retracted as shown in FIGS. 4*b* to 4*d* so that it passes rearwardly within the device towards its distal end.

As the eyelets become level with the hook elements 11, the control loops are no longer pulled downwardly into the hook elements and can therefore start to become free of the hook elements, as shown in FIGS. 4*b* and 4*c*. Then at FIG. 4*d* the control loops are no longer hooked around the hook elements so can run through the eyelets as the delivery apparatus is retracted.

The head element design removes the requirement for release wires in the attachment method and releases the device at the same time as the delivery system is removed from the patient, with no additional actions required from the user.

As described above, this may be achieved this by increasing the length of the control loops and incorporating two hooks, one at either side of the head element or tip, co-linear with the control loops. To assemble the device to the delivery system the control loops are fed through the eyelets before the free ends are attached to the hooks on the tip.

When the device eyelets are lower than the tip, the control loops will stay attached to the hooks. The device will therefore stay attached to the delivery system during compaction and unsheathing. However, when the tip is moved lower than the eyelets (e.g. when the delivery system is removed from the device), the control loops will detach from the hooks, allowing them to pull out of the eyelets and freeing the device from the delivery system.

The configuration of the present invention as such means that a separate mechanical step is not required as the apparatus is withdrawn. The device is released merely by withdrawing the head element, i.e. the delivery system tip.

In this connection, the hooks elements are axially fixed in place on the delivery system tip, and it is the relative position of the graft, with respect to the hooks, that fixes or releases the device.

In this connection, the hooks elements/slots should preferably be: —integrated onto the delivery system; above the level of the device; angled towards the device so that the 'closed' portion of the hook/slot is closest to the device; and open at one end so the control loops are free to leave. The control loops are preferably: —attached to the delivery system at one end (with the other end free); and long enough to loop through the eyelets and attach onto the hooks. The eyelets preferably are attached to the device.

A second embodiment of the present invention is described in relation to FIGS. 5*a* to 5*e*.

In this embodiment, control loops 30 are attached to the peaks 31 of the 1st ring of the medical device. When assembling the device to the delivery system, the control loops simply latch onto the hook elements 32 provided on the tip. This attachment method functions in the same way as above in relation to the first embodiment (the relative position of the tip with regard to the control loop attachment point would dictate whether or not the device was attached to the delivery system). However, this embodiment would leave control loops attached to the device in situ.

The hook elements may be provided with a secondary feature that allows them to be removed from the head element or tip, leaving the control loops free to pull out of the eyelets. This would aid in any circumstance in which the control loops became caught on the hook elements preventing the device from releasing.

FIGS. 6*a* to 6*c* shows a third embodiment where the hook elements 40 are able to be retracted in order to release the device.

As shown in the fourth embodiment of FIGS. 7*a* and 7*b*, the hook elements 50 may be angled or shaped such that rotation of the head element 11 also causes or facilitates the control loops to exit the hooks.

The control loops 52 may run the length of the delivery system so that they can be cut and removed, freeing the device from the delivery system. This would act as a failsafe if the control loops got caught in the hook elements.

The various embodiments of the present invention maintain the advantages of tethering the top of the medical device to the delivery system for more accurate deployment and easier manufacturing, but they remove any additional steps required by the user to detach the device from the delivery system, such as removing release wires, top cap, etc. associated with known methods.

The invention claimed is:

1. A medical device delivery apparatus, the apparatus comprising:

a head element at a proximal end of the apparatus, the head element extending through a medical device and projecting proximally therefrom;

the head element having a first hook element and a second hook element axially fixed in relation to the head element;

a first control loop and second control loop coupled to the medical device, the first control loop and the second control loop, each having a first end attached to the head element at a respective attachment point and a second free end configured to engage with the first and second hook elements, respectively.

2. Apparatus according to claim 1, wherein the first and second hook elements are forward facing, with a free end of each hook element extending in a direction towards a proximal portion of the head element.

3. Apparatus according to claim 1, wherein the first and second hook elements are provided at diametrically opposite sides of the head element.

4. Apparatus according to claim 1, wherein the first and second hook elements extend proximally to project radially outwardly from a longitudinal profile of the head element.

5. Apparatus according to claim 1, wherein the first and second hook elements are provided at a distal end of the head element.

6. Apparatus according to claim 1, wherein the first and second hook elements each take the form of an inclined slot, open at a proximal end and closed at a distal end.

7. Apparatus according to claim 6, wherein each slot has a tapering profile.

8. Apparatus according to claim 1, wherein the head element comprises a head body and a head plate, the head plate being coupled to a distal end of the head body to define said first and second hook elements between the head body and the head plate.

9. Apparatus according to claim 8, wherein the head body is chamfered at its distal end to define said first and second hook elements.

10. Apparatus according to claim 1, wherein the second free end of the first and second control loop passes through a first and second eyelet attached to the medical device before engaging with the first and second hook elements, respectively.

11. Apparatus according to claim 10, wherein the attachment points are provided on the head element proximally of the first and second hook elements.

12. Apparatus according to claim 1, wherein the one or more first and second hook elements are moveable between deployed and un-deployed positions.

13. Apparatus according to claim 12, wherein the one or more first and second hook elements are pivotable between the deployed and undeployed positions.

14. Apparatus according to claim 12, wherein the one or more first and second hook elements are retractable so as to be substantially flush with a longitudinal profile of the apparatus.

15. Apparatus according to claim 1, wherein the first and second hook elements are profiled so that rotation of the head element promotes release of the first and second control loops engaged with the first and second hook elements, respectively.

16. Apparatus according to claim 15, wherein the first and second hook elements comprise an angled section having a radially extending portion, the radially extending portion being configured to engage the first and second control loop, respectively.

17. A medical device deployment system for deploying a medical device comprising:

a medical device delivery apparatus having a head element at a proximal end of the apparatus, the head being configured for extending through the medical device and projecting proximally therefrom, the head element having a first hook element and a second hook element for engaging a first control loop and second control loop coupled to the medical device, wherein the first and second hook elements are axially fixed in relation to the head element;

the first control loop and second control loop having a first end attached to the head element and a second free end configured to engage with the first and second hook elements, respectively.

* * * * *